United States Patent
Mammadov et al.

(10) Patent No.: US 8,940,953 B2
(45) Date of Patent: Jan. 27, 2015

(54) PROCESS FOR CONVERSION OF LOWER ALIPHATIC ETHERS TO AROMATICS AND LOWER OLEFINS

(71) Applicant: Saudi Basic Industries Corporation, Riyadh (SA)

(72) Inventors: Aghaddin Kh. Mammadov, Houston, TX (US); Ali Said Al-Khuraimi, Jeddah (SA)

(73) Assignee: Saudi Basic Industries Corporation, Riyadh (SA)

( * ) Notice: Subject to any disclaimer, the term of this patent is extended or adjusted under 35 U.S.C. 154(b) by 78 days.

(21) Appl. No.: 13/890,478

(22) Filed: May 9, 2013

(65) Prior Publication Data

US 2013/0303814 A1 Nov. 14, 2013

(30) Foreign Application Priority Data

May 14, 2012 (EP) .................................... 12003779

(51) Int. Cl.
| | | |
|---|---|---|
| *C07C 1/20* | (2006.01) | |
| *C07C 1/207* | (2006.01) | |
| *C07C 1/22* | (2006.01) | |
| *B01J 29/06* | (2006.01) | |
| *B01J 29/072* | (2006.01) | |
| *B01J 29/87* | (2006.01) | |
| *B01J 37/02* | (2006.01) | |
| *B01J 29/40* | (2006.01) | |

(52) U.S. Cl.
CPC . *C07C 1/22* (2013.01); *B01J 29/06* (2013.01); *B01J 29/072* (2013.01); *B01J 29/87* (2013.01); *B01J 37/02* (2013.01); *C07C 1/20* (2013.01); *B01J 29/405* (2013.01); *B01J 2229/186* (2013.01); *C07C 2529/40* (2013.01)
USPC .......................... 585/640; 585/639; 585/469

(58) Field of Classification Search
USPC ......................................... 585/639, 640, 469
See application file for complete search history.

(56) References Cited

U.S. PATENT DOCUMENTS

| | | |
|---|---|---|
| 4,180,689 A | 12/1979 | Davies et al. |
| 4,392,989 A | 7/1983 | Chu et al. |
| 4,590,321 A | 5/1986 | Chu |
| 4,621,161 A | 11/1986 | Shihabi |
| 4,686,312 A | 8/1987 | Chu et al. |
| 4,724,270 A | 2/1988 | Chang et al. |
| 4,822,939 A | 4/1989 | Chu |
| 7,186,872 B2 | 3/2007 | Juttu et al. |

FOREIGN PATENT DOCUMENTS

| | | |
|---|---|---|
| EP | 0124999 A2 | 11/1984 |
| GB | 1446522 | 8/1976 |
| WO | 03002494 A1 | 1/2003 |

OTHER PUBLICATIONS

Extended European Search Report for Application No. 12003779.1; Date of Mailing: Oct. 5, 2012; 9 Pages.
Kirk-Othmer Encyclopedia of Chemical Technology Fourth Edition, vol. 10; Explosives and Propellants to Flame Retardants for Textiles; 1993; 20 pages.
Kirk-Othmer Encyclopedia of Chemical Technology Fifth Edition, vol. 16, 2006; 24 pages.
H.G. Karge et al. "Post Synthesis Modification I" Molecular Sieves, vol. 3 eds. (2002); pp. 204-255; 64 pages.

*Primary Examiner* — Thuan D Dang
(74) *Attorney, Agent, or Firm* — Cantor Colburn LLP

(57) ABSTRACT

The invention relates to a process for converting a feed stream consisting of reactive components and an optional feed diluent to a product stream comprising aromatic hydrocarbons and C2-C3 olefins, wherein the reactive components comprise at least 90 vol % of an aliphatic ether selected from the group consisting of methyl tertiary butyl ether and ethyl tertiary butyl ether, the process comprising the step of contacting the feed stream with a catalyst composition comprising a zeolite catalyst, wherein the zeolite catalyst is a zeolite modified by Ga and an element M1 selected from the group consisting of Zn, Cd and Cu.

17 Claims, No Drawings

PROCESS FOR CONVERSION OF LOWER ALIPHATIC ETHERS TO AROMATICS AND LOWER OLEFINS

This application claims priority to European Application No. 12003779.1, filed May 14, 2012, which is incorporated herein by reference in its entirety.

The invention relates to a process for converting a feed stream comprising lower aliphatic ethers to a product stream comprising aromatic hydrocarbons and lower olefins in the presence of a zeolite catalyst.

U.S. Pat. No. 4,724,270 discloses a process for converting a feed stream comprising oxygenated lower aliphatic hydrocarbon compound to a product stream comprising aromatic hydrocarbons by contacting the feed, particularly methanol or dimethylether with an acidic zeolite catalyst which has been treated at a temperature of higher than 725° C.; has a constraint index of 1 to 12 and a silica/alumina ratio of at least 12. The examples show aromatic hydrocarbons yields of about 28.9 wt % when converting methanol and 8 wt % when converting DME.

Benzene (B), toluene (T), and the xylenes (X) are useful as intermediates in the preparation of gasoline/distillate in the petrochemical industry or as valuable chemical feedstock. BTX are also utilized as a booster to enhance the octane number in gasoline. Since they are often produced in the same process, they can be considered a group, i.e., BTX.

Aliphatic oxygenates in general can be converted into a mixture containing aromatics like BTX, in the presence of various zeolite-type catalysts as described in the literature. For example, U.S. Pat. No. 4,590,321 discloses a process for converting $C_2$-$C_{12}$ hydrocarbons, e.g. propane and propylene; and oxygenates such as $C_1$-$C_5$ alcohols, e.g. methanol; or $C_2$-$C_6$ ethers, e.g. dimethylether, to aromatic hydrocarbons, in the presence of a zeolite catalyst having the structure of ZSM-5 or ZSM-11 and being modified with phosphorous oxide, under aromatization conditions including a temperature of 200-700° C., a pressure of 0.1-60 atm, a weight hourly space velocity (WHSV) of 0.1-400 and a hydrogen/hydrocarbon mole ratio of 0-20. The examples show BTX yields of at most 31.7 wt % obtained by converting methanol.

In U.S. Pat. No. 4,822,939 a process for converting oxygenates to aromatics is described, comprising a step of contacting the feed with a catalyst composition comprising a aluminosilicate zeolite containing at least 0.2 mass % of gallium, at temperature of 500-650° C., pressure of up to 3.5 MPa and weight hourly space velocity of 1-10. More specifically, U.S. Pat. No. 4,822,939 teaches to use a Ga-containing ZSM-5 type zeolite, having a Si/Al ratio of 5000-35000 before Ga-exchange, to catalytically convert $C_1$-$C_4$ aliphatic oxygenates into $C_2$-$C_5$ olefins with improved yields and reduced formation of $C_1$-$C_5$ paraffins.

U.S. Pat. No. 4,621,161 also discloses a process for converting oxygenates to aromatic hydrocarbons, in the presence of a steam-treated zeolite catalyst having a silica/alumina mole ratio of at least 100/1. When alcohol or ether feeds are used in this process, $C_2$-$C_5$ hydrocarbons and aromatics, such as durene, are produced.

In U.S. Pat. No. 4,724,270, lower olefins are obtained as well as BTX. The lower olefins obtained are not obtained in a selective manner.

It is an object of the present invention to provide a process for converting a feed stream comprising a lower aliphatic ether to a product stream comprising aromatic hydrocarbons and lower olefins with a high selectivity.

This object is achieved according to the invention by employing a process for converting a feed stream comprising an aliphatic ether selected from the group consisting of methyl tertiary butyl ether and ethyl tertiary butyl ether to a product stream comprising aromatic hydrocarbons and C2-C3 olefins, comprising the step of contacting the feed stream with a catalyst composition comprising a zeolite catalyst, wherein the zeolite catalyst is a zeolite modified by Ga and an element M1 selected from the group consisting of Zn, Cd and Cu.

The feed stream consists of reactive components and an optional diluent. Preferably, at least 90 vol % of the reactive components is methyl tertiary butyl ether and/or ethyl tertiary butyl ether.

According to the process of the present invention, not only BTX is produced but also a high selectivity towards C2-C3 olefins is shown. Hence, the product stream obtained comprises higher amount of valuable olefins and lower amount of non-desirable olefins. Furthermore, the overall performance of such process is stable over time, and very little coke formation was observed by employing the process of present invention. Moreover, the yield of aromatics in the process according to the invention is high.

Oxygenates and especially methyl tertiary butyl ether (MTBE) and ethyl tertiary butyl ether (ETBE) are common additives used in gasoline to improve combustion and reduce exhaust emissions. MTBE and ETBE are generally added to gasoline to lower the carbon monoxide emissions. However, the demand for MTBE and ETBE as gasoline additive has considerably declined in the recent years in response to environmental and health concerns. Therefore, it is an advantage of the process according to present invention that MTBE and ETBE can be effectively used to produce aromatic hydrocarbons and C2-C3 olefins with high selectivity.

MTBE and ETBE are commercially available chemical compounds, well-known for the person skilled in the art. An overview of their structure, properties and manufacture methods are for example given by the chapter on Ethers in Kirk-Othmer Encyclopedia of Chemical Technology, volume 10, page 567-583, DOI: 10.1002/0471238961.0516152407011414.a01.pub2.

The reactive component(s) in the feed stream may substantially consist of methyl tertiary butyl ether and/or ethyl tertiary butyl ether, for example at least 90 vol %, at least 95 vol % or at least 99 vol %. It will be appreciated by the skilled person that the term 'reactive components' is understood to mean the components in the feed stream which can react with the zeolite catalyst, such as hydrocarbons. Preferably, substantially all the aliphatic ether in the feed stream is methyl tertiary butyl ether as this results in a high aromatics yield and very little coke formation.

The invention provides a process for converting a feed stream comprising reactive components and an optional diluent to a product stream comprising aromatic hydrocarbons and C2-C3 olefins, wherein preferably at least 90 vol %, more preferably at least 95 vol % or most preferably at least 99 vol % of the reactive components is methyl tertiary butyl ether.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons. The aromatic hydrocarbons produced in the process of the present invention include benzene, toluene and xylenes, preferably benzene.

The term "olefin" is meant a hydrocarbon of formula $C_nH_{2n}$. C2 olefin means ethylene and C3 olefin means propylene.

The term 'feed stream' is meant the flow of reactants into the reactor, which comprise methyl tertiary butyl ether and/or ethyl tertiary butyl ether. The term 'product stream' is meant the output flow of products from the reactor, which comprise aromatic hydrocarbons and C2-C3 olefins.

The zeolite used in the process according to the invention can comprise crystalline or amorphous zeolite structures with crystalline materials being preferred, because of their more homogeneous pore size and channeling framework structures.

As used herein, the term "zeolite" or "aluminosilicate zeolite" relates to an aluminosilicate molecular sieve. These inorganic porous materials are well known to the skilled person. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001).

Aluminosilicate zeolites are generally characterized by the Si/Al ratio of the framework. This ratio may vary widely in the catalyst composition used in the process according to the invention. Preferably, the Si/Al ratio is from about 5 to 1000, preferably from about 8 to 500 or preferably from 10 to 100 or more preferably from 10 to 200. Any aluminosilicate that shows activity in converting alkanes to aromatic hydrocarbons, before modifying it with a specific metal, may be applied. Examples of suitable materials include the mordenite framework inverted (MFI) and other zeolite structures known to the skilled person, for example MEL, MWW, BEA, MOR, LTL and MTT type. Preferred materials are those known as ZSM-5, ZSM-11, ZSM-8, ZSM-12, ZSM-22, ZSM-23, ZSM-35, ZSM-38, and beta aluminosilicates. Most preferably the zeolite is a MFI type zeolite, for example a ZSM-5 zeolite.

The term "medium pore zeolite" is commonly used in the field of zeolite catalyst compositions. A medium pore size zeolite is a zeolite having a pore size of 5-6 Å. Suitable medium pore size zeolites are 10-ring zeolites. i.e. the pore is formed by a ring consisting of 10 $SiO_4$ tetrahedra. Zeolites of the 8-ring structure type are called small pore size zeolites; and those of the 12-ring structure type, like for example beta zeolite, are referred to as large pore sized. In the above cited Atlas of Zeolite Framework Types, various zeolites are listed based on ring structure. Preferably, the zeolite is a medium pore size aluminosilicate zeolite.

The zeolite of the present invention may be dealuminated. Preferably, the silica ($SiO_2$) to alumina ($Al_2O_3$) molar ratio of the ZSM-5 zeolite is in the range of 10 to 200. Means and methods to obtain dealuminated zeolite are well known in the art and include, but are not limited to the acid leaching technique; see e.g. Post-synthesis Modification I; Molecular Sieves, Volume 3; Eds. H. G. Karge, J. Weitkamp; Year (2002); Pages 204-255. Preferably, the zeolite is a dealuminated zeolite having a $SiO_2$ to $Al_2O_3$ molar ratio of 10 to 200, for improving the performance/stability of the catalyst composition. Means and methods for quantifying the $SiO_2$ to $Al_2O_3$ molar ratio of a dealuminated zeolite are well known in the art and include, but are not limited to AAS (Atomic Absorption Spectrometer) or ICP (Inductively Coupled Plasma Spectrometry) analysis.

It is preferred that the zeolite is in the hydrogen form: i.e. having at least a portion of the original cations associated therewith replaced by hydrogen. Methods to convert an aluminosilicate zeolite to the hydrogen form are well known in the art. A first method involves direct ion exchange employing an acid. A second method involves base-exchange using ammonium salts followed by calcination.

The zeolite catalyst used in the process according to the present invention is a zeolite modified by Ga and an element M1 selected from the group consisting of Zn, Cd and Cu that allows the combination of a high yield of aromatics and a high selectivity towards olefins having from 2 to 3 carbon atoms.

Presence of Ga was found to increase aromatics production from lower aliphatic ethers. The amount of Ga in the zeolite catalyst was found to influence the selectivity of the catalyst to form aromatics from lower aliphatic ethers. Preferably, for increasing the selectivity, the zeolite catalyst contains therefore at least 0.1, 0.5, 1, 1.5, 2 or even 3 wt % of Ga. If the zeolite would contain too high an amount of Ga, the pores of the zeolite might become at least partly clogged, resulting in a masking effect. The Ga-content of the catalyst is thus preferably at most 10, 8, 7.5, 7, 6.5 or even at most 5 wt % of Ga. Accordingly, the preferred range of Ga in the zeolite catalyst is 0.1-10 wt %.

The gallium element and the element M1 contained in the zeolite catalyst according to the invention may be present in the zeolite structure as framework or non-framework element; as counterion in the zeolite; on its surface, e.g. in the form of metal oxides; or be present in a combination of these forms.

The position of gallium in the zeolite structure is determined by the method by which gallium is introduced to the zeolite. $Ga_2O_3$ modification of ZSM-5 zeolite catalyst using the impregnation method leads to the formation of separate oxide phase deposited on the surface. The gallium oxide phase in the form of individual active centres participates in the formation of carbocation intermediates during the contact process according to the invention. Insertion of gallium by ion exchange methods leads to the formation of the catalyst composition differing only by gallium dispersion. Preferably the gallium is present in the MFI type zeolite framework.

Preferably, the catalyst used in present process has the framework structure of ZSM-5 with Bronsted acid sites provided by tetrahedrally coordinated gallium/M1 in the framework structure and silicon. Best catalyst is obtained when only some Al in the framework is substituted by Ga/M1.

Preferably the amount of the element M1 selected from the group consisting of Zn, Cd and Cu in the zeolite catalyst is 0.1-5 wt %.

Preferably, the amount of Zn with respect to the total amount of the element M1 in the zeolite catalyst is 50-100 wt %, more preferably 60-100 wt %, more preferably 75-100 wt %, more preferably 90-100 wt %, more preferably 95-100 wt %.

Preferably, the zeolite is ZSM-5 zeolite, the amount of Ga in the zeolite catalyst is 0.1-10 wt %, the amount of the element M1 in the zeolite catalyst is 0.1-5 wt % and the amount of Zn with respect to the total amount of the element M1 in the zeolite catalyst is 50-100 wt %.

The zeolite catalyst used in the present process can be prepared by suitable methods of preparing and modifying zeolites as well known to the skilled person; including for example impregnation, calcination, steam and/or other thermal treatment steps. Such methods are disclosed for instance in documents U.S. Pat. No. 7,186,872B2; U.S. Pat. No. 4,822,939 and U.S. Pat. No. 4,180,689 hereby incorporated by reference.

The catalyst composition comprises a zeolite catalyst as described above. The catalyst composition may consist of the zeolite catalyst as described above, or the catalyst composition may comprise further components such as diluents or binders or other support materials. Preferably these further components do not negatively affect the catalytic performance of the catalyst composition of the invention. Such components are known to the skilled person.

For example, the catalyst composition of the invention may further comprise a non-acidic inert diluent. Preferably the non-acidic inert diluent is silicon oxide.

Examples of suitable support or binder materials include metal oxides, mixed metal oxides, clays, metal carbides and metal oxide hydroxides. The metal oxide or the mixed metal oxides may be chosen from the group of metal oxides comprising for example, oxides of magnesium, aluminium, titanium, zirconium and silicon. The clay may be, but is not limited to, kaolin, montmorillonite or betonite. Metal carbides suitable for use in the composition of the invention are, for example, molybdenum carbide and silicon carbide. The metal oxide hydroxide may be feroxyhyte or Goethite, or more preferably boehmite.

The binder may be present in the composition according to the invention in for example at least 5 wt %, for example at least 10 wt %, for example at least 20 wt %, for example at least 30 wt %, for example at least 40 wt %, for example at least 50% and/or for example at most 5 wt %, for example at most 10 wt %, for example at most 20 wt %, for example at most 30 wt %, for example at most 40 wt %, for example at most 50 wt % with respect to the total catalyst composition.

If the zeolite catalyst composition is to contain a binder, such catalyst composition can be obtained, for example, by mixing the modified zeolite and a binder in a liquid, and forming the mixture into shapes, like pellets or tablets, applying methods known to the skilled person.

The feed stream may further contain one or more diluents, the concentration of which may vary over wide ranges; preferably the feed stream comprises 10-90 vol % of a feed diluent. Examples of suitable diluents include helium, nitrogen, carbon dioxide, and water.

The step of contacting the feed stream with the zeolite catalyst composition can be performed in any suitable reactor, as known to a skilled man, for example in a fixed bed, a fluidized bed, or any other circulating or moving bed reactor.

With reactor is meant a device for containing and controlling a chemical reaction, in the case of oxidative and non-oxidative dehydrogenation reaction to form an alkene from the corresponding alkane.

The contacting step in the process according to the present invention is performed at lower aliphatic ether aromatization conditions. These conditions are known from the prior art. A higher temperature generally enhances conversion to aromatics. However, higher temperatures may induce side-reactions or promote deactivation of the catalyst. The Intermediate reactions during this conversion is the olefin formation step which requires selection of the suitable temperature conditions to get these intermediates with high selectivity Therefore, the contacting step is preferably, performed at a temperature of 450-650° C. Even more preferably, the contacting step is performed at a temperature of 550-600° C.

Suitable pressures to conduct the contacting step are from between the atmospheric pressure to 3 MPa, preferably pressure is below about 2.5, 2.0, 1.5, 1.0, 0.5 or even below 0.3 MPa.

The flow rate at which the feed stream is fed to the reactor may vary widely, but is preferably such that a weight hourly space velocity (WHSV) results of about 0.1-100 $h^{-1}$, more preferably WHSV is about 0.5-50 $h^{-1}$, or 1-20 $h^{-1}$ or most preferably 1.5-1.8 $h^{-1}$. The WHSV may be preferably at least 0.1 $h^{-1}$, for example at least 10 $h^{-1}$, for example at least 20 $h^{-1}$, for example at least 30 $h^{-1}$ and/or for example at most 1 $h^{-1}$, for example at most 10 $h^{-1}$, for example at most 20 $h^{-1}$, for example at most 30 $h^{-1}$, for example at most 40 $h^{-1}$, for example at most 50 $h^{-1}$. WHSV is the ratio of the rate at which the feed stream is fed to the reactor (in weight or mass per hour) divided by the weight of catalyst composition in a reactor; and is thus inversely related to contact time. By contact time is meant the period of time during which the feedstream is in contact with the catalyst composition.

The WHSV indicates that there is a certain rate at which the feedstream is fed to the reactor. The total length of time in which the feedstream is fed to the reactor is known as the "Time-on-Stream (TOS)." The TOS may be for example at least 50 hours, for example at least 75 hours, for example at least 100 hours, for example at least 150 hours and/or for example at most 50 hours, for example at most 75 hours, for example at most 100 hours, for example at most 150 hours, for example at most 200 hours. For example the TOS for a catalyst composition according to the invention during which time the catalyst composition maintains its activity in terms of a high conversion and high selectivity for benzene, ranges from for example 50 to 200 hours, for example from 100 to 150 hours.

The present invention further describes a zeolite modified by Ga and an element M1 selected from the group consisting of Zn, Cd and Cu, comprising 0.1-10 wt % of Ga and 0.1-5 wt % of the element M1.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will now be further illustrated with below described experiments.

Comparative Experiment 1

In this example the conversion of MTBE using Ga-modified zeolite catalyst was tested.

An MFI type zeolite (Si/Al-60) was impregnated with a suitable amount of gallium nitrate so that the amount of Ga in the zeolite catalyst would be 3 wt %. Water evaporation was followed by drying at 120° C. for 12 hours. The solid material then was calcined at 400° C. for 4 hours. Before the reaction the catalyst was treated with air at reaction temperature for 2 hours and treated with water for 30 min.

A tubular quartz fixed bed reactor with inner diameter of 1.2 cm was loaded with 2 ml of the gallium catalyst of particles size of 40-60 mesh. The reaction was conducted at 560° C. and pressure of 1 atmosphere at a weight hourly space velocity (WHSV) of 1.6 $h^{-1}$ with respect to the MTBE feed. $N_2$ gas was passed through the reactor with a flow rate of 30 ml/min, followed after about 1 hour by liquid MTBE with a flow rate of 0.03 ml/min. Product stream composition was analysed by standard GC techniques after 15, 30 and respectively 70 min of reaction. The results are summarized in Table 1.

"Conversion MTBE" is defined herein as the mole of converted amount of MTBE divided by the mole of supplied amount of MTBE and multiplied by 100.

"Total olefins yield" is defined herein as the mole of the total olefins in the product divided by the MTBE conversion (in mole %) and multiplied by 100.

"Total aromatics yield" is defined herein as the mole of the total aromatics in the product divided by the MTBE conversion (in mole %) and multiplied by 100. These above mentioned parameters on the basis of GS analysis were measured as follows:

TABLE 1

| Product composition, | Time of reaction, min | | |
|---|---|---|---|
| % mole | 15 | 30 | 70 |
| Benzene | 4.60 | 7.19 | 7.69 |
| Xylene | 3.11 | 3.58 | 2.64 |
| Ethylene | 1.46 | 0.44 | 0.35 |
| Propylene | 0.30 | 0.25 | 0.20 |
| Methane | 13.60 | 14.90 | 14.00 |
| Ethane | 5.80 | 6.12 | 5.72 |
| Propane | 2.86 | 0.21 | 0.13 |
| Hydrogen | 24.00 | 27.60 | 28.30 |
| Conversion MTBE, % mole | 100 | 100 | 100 |
| Total olefins yield, % mole | 4.5 | 2.5 | 2.0 |
| Total aromatics yield, % mole | 56.9 | 60.4 | 60.1 |

Example 1

In this example the conversion of MTBE using a zeolite catalyst according to the present invention was tested.

The zeolite catalyst used in this example 1 was prepared in the same way as in Comparative experiment 1, except that the MFI type zeolite was additionally modified by Zn. The MFI type of ZSM-5 during preparation was impregnated simultaneously by $Ga(NO_3)_3$ and $Zn(NO_3)_2$ and then dried at 120° C. and calcined as in comparative experiment 1. The final catalyst has a composition 3% Ga-1% Zn/ZSM-5.

The conversion of MTBE was performed in the same way as in the comparative experiment 1, but using the 3% Ga-1% Zn/ZSM-5 catalyst. The results are summarized in Table 2.

TABLE 2

| Product composition, | Time of reaction, min | |
|---|---|---|
| % mole | 15 | 55 |
| Benzene | 2.77 | 3.56 |
| Toluene | 0.80 | 1.58 |
| Xylene | 2.76 | 3.0 |
| Ethylene | 8.27 | 9.0 |
| Propylene | 4.16 | 4.19 |
| Methane | 8.18 | 6.88 |
| Ethane | 5.42 | 6.60 |
| Propane | 12.10 | 9.40 |
| Hydrogen | 20.8 | 20.0 |
| Conversion MTBE, % mole | 97.5 | 97.8 |
| Total olefins yield, % mole | 20.2 | 19.8 |
| Total aromatics yield, % mole | 31.2 | 37.8 |

The results summarized in Table 1 and 2 indicate stable aromatics production during the experiments; and aromatic yields of even 60% at 100% MTBE conversion. The amount of ethylene and propylene produced by the example 1 is much higher than by the comparative experiment 1. In addition, no change in overall performance and no pressure drop in the reactor were observed even after 8 hours of reaction. This also indicates no coke formation during the process of present invention.

Example 2

Example 2 was carried out as in Comparative experiment 1, but using as a feed ETBE which was converted at the condition of Example 1 using zeolite based catalyst 3% Zn-1% Ga-2% Cd/ZSM-5, containing in addition Cd but with different content of Ga and Zn. The catalyst in the case of ETBE is more stable than that of MTBE, therefore within 2 hours of operation there was not observed significant change of catalyst performance. The results are summarized in Table 3, below.

TABLE 3

| Product composition, | Time of reaction, hour | |
|---|---|---|
| % mole | 1 h | 2 h |
| Benzene | 2.40 | 2.80 |
| Toluene | 0.58 | 1.25 |
| Xylene | 1.65 | 1.80 |
| Ethylene | 11.15 | 10.20 |
| Propylene | 6.20 | 6.85 |
| Methane | 6.14 | 7.20 |
| Ethane | 7,.30 | 8.10 |
| Propane | 13.6 | 12.30 |
| Hydrogen | 22.50 | 23.61 |
| N2 | Bal | Bal |
| Conversion ETBE, % mole | 98.2 | 95.5 |
| Total olefins yield, % mole | 24.6 | 23.2 |
| Total aromatics yield, % mole | 29.5 | 32.3 |

The invention claimed is:

1. A process for converting a feed stream comprising reactive components and an optional feed diluent to a product stream comprising aromatic hydrocarbons and $C_2$-$C_3$ olefins, the process comprising:
   contacting the feed stream with a catalyst composition comprising a zeolite catalyst, wherein the zeolite catalyst is a zeolite modified by Ga and an element M1 selected from the group consisting of Zn, Cd and Cu; and
   converting the feed stream to the product stream comprising aromatic hydrocarbons and $C_2$-$C_3$ olefins, wherein the reactive components comprise at least 90 vol % of an aliphatic ether selected from the group consisting of methyl tertiary butyl ether and ethyl tertiary butyl ether.

2. The process according to claim 1, wherein the aliphatic ether in the feed stream is methyl tertiary butyl ether.

3. The process according to claim 1, wherein the zeolite is ZSM-5 zeolite.

4. The process according to claim 1, wherein the amount of Ga in the zeolite catalyst is 0.1-10 wt %.

5. The process according to claim 1, wherein the amount of the element M1 in the zeolite catalyst is 0.1-5 wt %.

6. The process according to claim 1, wherein the amount of Zn with respect to the total amount of the element M1 in the zeolite catalyst is 50-100 wt %.

7. The process according to claim 1, wherein the catalyst composition further comprises a catalyst support or a catalyst binder.

8. The process according to claim 1, wherein the feed stream comprises 10-90 vol % of the feed diluent.

9. The process according to claim 1, wherein the contacting step is performed at a temperature of 450-650° C.

10. The process according to claim 1, wherein the contacting step is performed at a pressure between the atmospheric pressure to 3 MPa.

11. The process according to claim 1, wherein the contacting step is performed at WHSV from 0.1 to 100 h$^{-1}$.

12. The process of claim 9, wherein the temperature is 550-600° C.

13. A process for converting a feed stream comprising reactive components and an optional feed diluent to a product stream comprising aromatic hydrocarbons and $C_2$-$C_3$ olefins, the process comprising:
  contacting the feed stream with a catalyst composition comprising a zeolite catalyst, wherein the zeolite catalyst is a zeolite modified by Ga and an element M1 selected from the group consisting of Zn, Cd and Cu, wherein the amount of Ga in the zeolite catalyst is 0.1-10 wt %; and
  converting the feed stream to the product stream comprising aromatic hydrocarbons and $C_2$-$C_3$ olefins, wherein the reactive components comprise at least 90 vol % of an aliphatic ether selected from the group consisting of methyl tertiary butyl ether and ethyl tertiary butyl ether.

14. The process of claim 13, wherein the amount of Zn with respect to the total amount of the element M1 in the zeolite catalyst is 50-100 wt %.

15. The process of claim 13, wherein the contacting step is performed at a temperature of 450-650° C., a pressure between the atmospheric pressure to 3 MPa, and WHSV from 0.1 to 100 h$^{-1}$.

16. The process of claim 1, wherein the feed stream consists of the reactive components and optionally the feed diluent.

17. The process of claim 13, wherein the feed stream consists of the reactive components and optionally the feed diluent.

* * * * *